United States Patent [19]
Raunig

[11] Patent Number: 5,817,039
[45] Date of Patent: Oct. 6, 1998

[54] NASAL SPLINT SYSTEM

[76] Inventor: Hermann Raunig, Bahnhofstrasse 13, Spittal/Drau, Australia, 9800

[21] Appl. No.: 662,258

[22] Filed: Jun. 14, 1996

[30] Foreign Application Priority Data

Jan. 24, 1996 [AU] Australia .................................. 110/96

[51] Int. Cl.$^6$ ...................................................... A61F 5/00
[52] U.S. Cl. ........................... 602/5; 602/17; 606/204.45; 128/858
[58] Field of Search .................................. 602/5, 6, 7, 8, 602/17, 61, 902; 606/196, 199, 201, 204.45; 128/201.18, 858; D24/189; 2/9, 431

[56] References Cited

U.S. PATENT DOCUMENTS

| | | | |
|---|---|---|---|
| 1,372,089 | 3/1921 | Rostow | 602/17 X |
| 1,378,455 | 5/1921 | Hilgers | 602/17 X |
| 4,274,404 | 6/1981 | Shippert | 128/858 |
| 4,340,040 | 7/1982 | Straith . | |
| 4,734,320 | 3/1988 | Ohira et al. | 602/75 |
| 5,012,527 | 5/1991 | Michel | 2/9 |
| 5,022,389 | 6/1991 | Brennan | 128/858 |

*Primary Examiner*—Richard J. Apley
*Assistant Examiner*—Kim M. Lee
*Attorney, Agent, or Firm*—Jacobson, Price, Holman & Stern, PLLC

[57] ABSTRACT

Nasal splint system comprising a nasal splint (6) with a central part designed to rest on the bridge of the nose and two lateral parts designed to rest on each side on the cheek adjacent the nose, wherein the nasal splint (6) is adaptable to the individual form of the nose of a patient and can be fixed, if necessary, additionally with a forehead support (7) consisting of a transversal part (8) designed to rest on the forehead (15) and a central part (9) designed to rest on the nasal splint (6). The nasal splint (6) and/or the forehead support (7) are formed of a compound structure consisting of an intermediate flexible layer, of a foam rubber layer adjacent the nose being covered by a skin-compatible adhesive layer, and of a layer covering the adhesive layer. The fixation of the nasal splint (6) may be effected by means of skin-compatible adhesive tapes (11) on the left cheek and of the right cheek and, if necessary, by means of a forehead support (7), which is also fixed by adhesive tapes (17). (FIG. 5)

19 Claims, 1 Drawing Sheet

NASAL SPLINT SYSTEM

FIELD OF THE INVENTION

The present invention refers to a nasal splint system comprising a nasal splint with a central part designed to rest on the bridge of the nose and two lateral parts designed to rest on each side on the cheek adjacent the nose, wherein the nasal splint is adaptable to the individual form of the nose of a patient and can be fixed, if necessary, additionally with a forehead support consisting of a transversal part designed to rest on the forehead and a central part designed to rest on the nasal splint.

BACKGROUND OF THE INVENTION

Until now splints formed from plaster, thermoplastic synthetics or light metal are known. Plaster on the nose is ugly and additionally soils both patient and surgeon during application. In spite of the fact that the quality of the thermoplastic synthetics has been improved, their use for nasal splints remains troublesome because for corrections the splint has to be warmed and then re-cooled. Moreover the presently available light metal and synthetic splints often do not reach the processus frontalis maxillae and therefore rest only on the bridge of the nose being itself mobile.

The nasal splint described in the U.S. Pat. No. 4,340,040 can be considered as prior art. It reveals a post-operative nasal splint consisting of a central part and two lateral parts composed of a flexible metal layer covered by a foam rubber layer. The flexibility allows the splint to be individually fitted. However it is not possible to consider this known splint as composed of layers of compound materials. Furthermore this known construction comprises several protruding parts which may cause further wounds or injuries when the patient hits a pillow when turning the head. In this case the impact energy will be transmitted directly to the bridge of the nose, which should be protected. Moreover the sling for placing a pad under the patient's nose is complicated and not easy to handle.

SUMMARY OF THE INVENTION

The task of the present invention is to create a nasal splint system providing a optimal support of the mobile bridge of the nose, wherein the nasal splint should not only cover the bridge as usual but also a facultative osteotomy gap in the processus frontalis maxillae when choosing the respective size. If necessary, an additional fixation by a forehead support should also be possible.

For solving this task according to the invention there is proposed a nasal splint system comprising a nasal splint with a central part designed to rest on the bridge of the nose and two lateral parts designed to rest on each side on the cheek adjacent the nose, wherein the nasal splint is adaptable to the individual form of the nose of a patient and can be fixed, if necessary, additionally with a forehead support consisting of a transversal part designed to rest on the forehead and a central part designed to rest on the nasal splint, wherein the nasal splint and/or the forehead support is formed of a compound structure consisting of an intermediate flexible layer, of a foam rubber layer adjacent the nose being covered by a skin-compatible adhesive layer and of a layer covering the adhesive layer.

The invention equally facilitates the plastic surgeon's task as well as saving him time, because it offers a nasal splint system providing a stable fixation with the support of the processus frontalis maxillae together with the three point fixation, either with adhesive tapes alone or, if necessary, with the additional stabilization of the forehead support. Furthermore the inventive compound structure allows an easy adaptation to the individual form of the nose of the patient. The inventive nasal splint system allows to protect the nose without any restrictions and minimizes any potential risks of injuries because there do not exist any protruding parts when the nasal splint is fixed.

The flexible layer may be composed of aluminium or other light-weight materials, which can be used in sterile environments during surgery. For providing protection of the flexible layer and also for allowing a better handling of the inventive nasal splint system, there is further proposed according to a preferred embodiment that the flexible layer is covered with a surface layer. Furthermore preferably the layer covering the adhesive layer is made of silicone paper.

For allowing a sufficient support of the mobile bridge of the nose and effectively preventing pain resulting from excessive pressure at particular positions of the nose there is preferably proposed that the thickness of the foam rubber layer is between 0.5 and 2 mm, in particular about 1 mm.

According to a further preferred embodiment the adhesive layer covers only parts of the nasal splint and/or the forehead support.

For an easy manufacture it is preferably proposed that the lateral parts of the nasal splint are formed as integral parts with the central part designed to rest on the bridge and wherein the distance of the two ends of the central part in a direction perpendicular to the orientation of the lateral parts is at least double the extension of the lateral parts in the same direction. The inventive dimensions of the central and lateral parts of the nasal splint furthermore allow a sufficient support in the central area and an easy adaptation on the cheeks adjacent the nose.

Since human noses rarely show straight outer contours of the nose the central part of the nasal splint is provided with at least one slit running in a direction parallel to the orientation of the lateral parts of the nasal splint according to a further preferred embodiment. Such slit allows an easier bending of the central part of the nasal splint when fitting it to the nose of a patient and further considering the fact that below the nasal splint there might be arranged bandages for covering wounds.

As already stated above an additional fixation by a forehead support may be necessary in certain cases. Therefore it is preferably proposed that the central part of the forehead support is provided with a further transversal part at the end being opposite of the transversal part designed to rest on the forehead, and wherein the further transversal part of the forehead support measures about 50% to 80%, in particular 60% to 75%, of the width of the central part of the nasal splint. Thereby the further transversal parts of the forehead support allows a good fixation on the central part of the nasal splint.

For providing the inventive nasal splint system in standard sizes it is further proposed that the distance between the central lines of the transversal parts of the forehead support is between 2.5 and 4.5 cm, in particular about 3 to 3.5 cm.

BRIEF DESCRIPTION OF THE DRAWINGS

The inventive nasal splint system is further described in more detail with an example being shown in the figures, wherein.

DETAILED DESCRIPTION OF THE PREFERRED EMBODIMENTS

Figure 1:
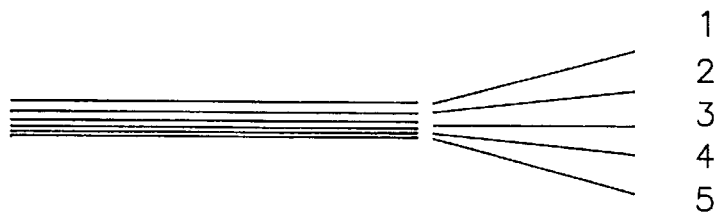
FIG. 1 shows a cross section of the inventive nasal splint system comprising a nasal splint and a forehead support, if necessary, to illustrate the composition of layers.
Figure 2:
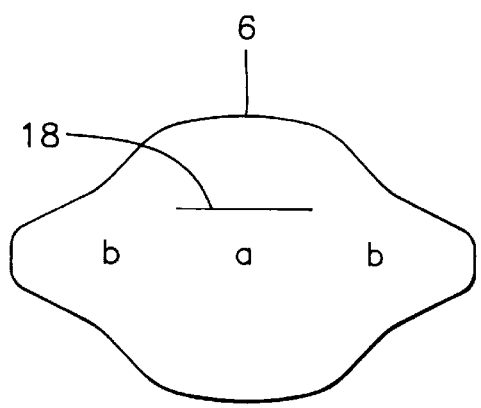
FIG. 2 shows a complete view of the inventive nasal splint.
Figure 3:
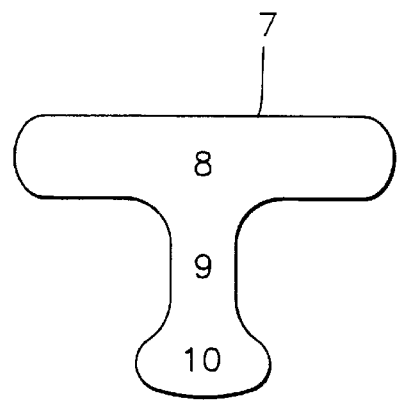
FIG. 3 shows a complete view of the inventive forehead support.

According to FIGS. 1 to 3, the nasal splint 6 and the forehead support 7 consist of layers of composite material with a surface layer 1, a flexible layer 2, a foam rubber layer 3 as cushioning, on which a skin-compatible adhesive layer 4 is formed on the inner side, and a covering layer 5 of silicone paper.

The surface layer 1 can be formed according to the requirements or may be omitted. The flexible layer 2 enables adaptation to the individual form of the nose and offers principal mechanical protection.

FIG. 2 shows a complete view of the nasal splint 6. It consists of a central part (a) designed to rest on the bridge of the nose and two lateral parts (b) designed to rest on the cheek on each side of the nose. In the central part (a) of the nasal splint 6 there is provided a slit 18 running in a direction parallel to the orientation of the lateral parts (b) of the nasal splint 6, for adapting the nasal splint 6 to the outer contours of the nose. The slit 18 may especially only be provided in the surface layer 1 and the flexible layer 2 and not in the other layers of the nasal splint 6. The nasal splint 6 can be fitted individually to the form of the nose of a patient. The size of the nasal splint depends on the size of the nose 16 and can be manufactured in standard sizes.

FIG. 3 shows a complete view of the forehead support 7. It consists of an upper transversal part 8, a smaller central part 9 and a lower transversal part 10. The size of the forehead support 7 depends on the size of the facial cranium and can be manufactured in standard sizes.

Figure 4:
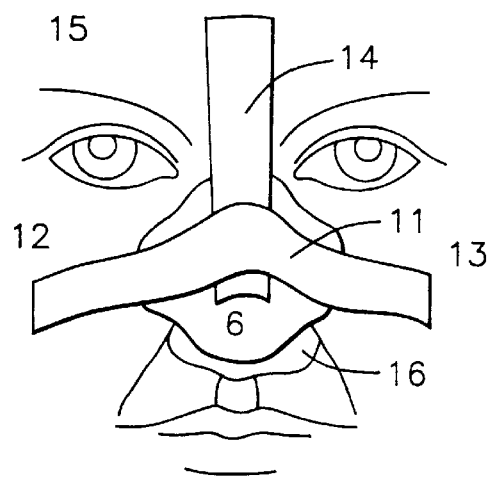
FIG. 4 shows the fixation of the splint on the left and right cheek as well as on the forehead.

FIG. 4 shows the fixation of the splint 6 on the left and right cheek as well as on the forehead. This fixation is effected by extensions of the adhesive tapes 11, 14 being formed on the surface layer 1, for the right cheek 12, for the left cheek 13 and for the forehead 15.

Figure 5:
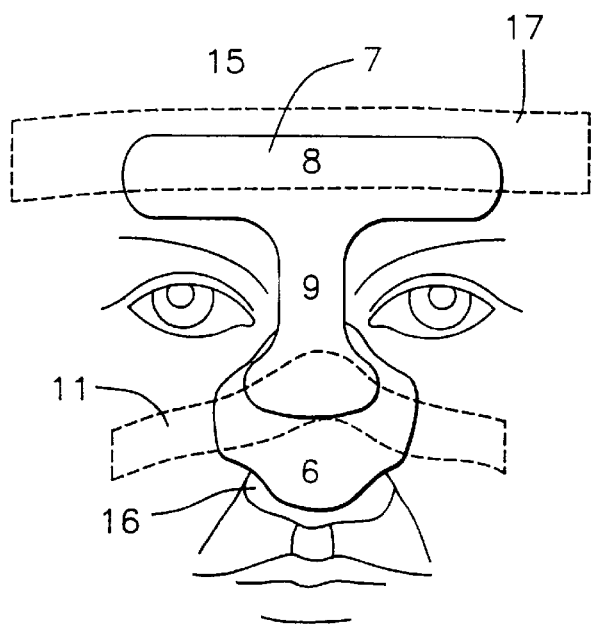
FIG. 5 shows the fixation of the inventive nasal splint on the left and right cheek and the stabilization by means of the inventive forehead support as well as the fixation by means of adhesive tapes on the forehead and the cheeks.

FIG. 5 shows the fixation of the nasal splint 6 on the left and right cheek as already shown in FIG. 3, further by means of an adhesive tape 17 across the forehead 15 and the upper transversal part of the forehead support 7 and additionally the fixation by means of the forehead support 7 which is adhered to the nasal splint 6.

I claim:

1. Nasal splint system comprising
   a nasal splint with a central part designed to rest on the bridge of the nose and two lateral parts designed to rest on each side on the cheek adjacent the nose, the nasal splint being adaptable to the individual form of the nose of a patient,
   a forehead support consisting of a transversal part designed to rest on the forehead and a central part designed to rest on, and assist to fix in place, the nasal splint,
   the nasal splint and the forehead support being formed of a compound structure consisting of an intermediate flexible layer, a foam rubber layer adjacent the nose being covered by a skin-compatible adhesive layer and a layer covering the adhesive layer.

2. Nasal splint system according to claim 1, wherein the flexible layer is covered with a surface layer.

3. Nasal splint system according to claim 1, wherein the layer covering the adhesive layer is made of silicone paper.

4. Nasal splint system according to claim 1, wherein the thickness of the foam rubber layer is between 0.5 and 2 mm.

5. Nasal splint system according to claim 1, wherein the adhesive layer covers only parts of the nasal splint and the forehead support.

6. Nasal splint system according to claim 1, wherein the lateral parts of the nasal splint are formed as integral parts with the central part designed to rest on the bridge and wherein a distance between two ends of the central part in a direction perpendicular to the orientation of the lateral parts is at least double an extension of the lateral parts in a same direction.

7. Nasal splint system according to claim 1, wherein the central part of the nasal splint is provided with at least one slit running in a direction parallel to the orientation of the lateral parts of the nasal splint.

8. Nasal splint system according to claim 1, wherein the central part of the forehead support is provided with a further transversal part at an end opposite to the transversal part designed to rest on the forehead, and wherein the further transversal part of the forehead support measures about 50% to 75% of the width of the central part of the nasal splint.

9. Nasal splint system according to claim 8, wherein the distance between central lines of the transversal parts of the forehead support is between 2.5 and 4.5 cm.

10. The nasal splint system according to claim 1, wherein the lateral parts of the nasal splint portion are formed as integral parts with the central part designed to rest on the bridge and wherein a distance between two ends of the central part in a direction perpendicular to the orientation of the lateral parts is at least double an extension of the lateral parts in a same direction.

11. The nasal splint system according to claim 1, wherein the central part of the nasal splint portion is provided with at least one slit running in a direction parallel to the orientation of the lateral parts of the nasal splint portion.

12. Nasal splint system comprising
    a nasal splint with a central part designed to rest on the bridge of the nose and two lateral parts designed to rest on each side on the cheek adjacent the nose, the nasal splint being adaptable to the individual form of the nose of a patient,
    a forehead support consisting of a transversal part designed to rest on the forehead and a central part designed to rest on, and assist to fix in place, the nasal splint,
    the nasal splint and the forehead support being formed of a compound structure consisting of an intermediate flexible layer, a foam rubber layer adjacent the nose being covered by a skin-compatible adhesive layer and a layer covering the adhesive layer,
    the central part of the forehead support being provided with a further transversal part at an end opposite to the transversal part designed to rest on the forehead, and the further transversal part of the forehead support measures about 50% to 80% of the width of the central part of the nasal splint.

13. Nasal splint system according to claim 12, wherein a distance between central lines of the transversal parts of the forehead support is between 2.5 and 4.5 cm.

14. Nasal splint system according to claim 13, wherein the distance between the central lines of the transversal parts of the forehead support is between 3 and 3.5 cm.

15. A nasal splint system comprising a nasal splint portion and a forehead support portion, the nasal splint portion including a central part designed to rest on the bridge of the nose and two lateral parts designed to rest on each side on the cheek adjacent the nose, the forehead support portion fixing the nasal splint portion to the nose of a patient, the forehead support portion including a transversal part designed to rest on the forehead and a central part connecting the transversal part of the forehead support portion and the central part of the nasal splint, the nasal splint portion and the forehead support portion being formed of a compound structure consisting of an intermediate flexible layer, a foam rubber layer adjacent the nose being covered by a skin-compatible adhesive layer and a layer covering the adhesive layer.

16. The nasal splint system according to claim 15, wherein the flexible layer is covered with a surface layer.

17. The nasal splint system according to claim 16, wherein the adhesive layer covers only parts of the nasal splint portion and the forehead support portion.

18. The nasal splint system according to claim 15, wherein the layer covering the adhesive layer is made of silicone paper.

19. The nasal splint system according to claim 15, wherein the thickness of the foam rubber layer is between 0.5 and 2 mm.

* * * * *